US009096562B2

(12) United States Patent
Rokicki et al.

(10) Patent No.: US 9,096,562 B2
(45) Date of Patent: Aug. 4, 2015

(54) EPOXIDATION PROCESS

(71) Applicant: Scientific Design Company, Inc., Little Ferry, NJ (US)

(72) Inventors: Andrzej Rokicki, Mountain Lakes, NJ (US); Jason Durand, Paramus, NJ (US); Rudy Anthony Morin, Dumont, NJ (US); Wojciech Suchanek, Wyckoff, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 13/950,973

(22) Filed: Jul. 25, 2013

(65) Prior Publication Data
US 2014/0031568 A1  Jan. 30, 2014

Related U.S. Application Data

(60) Provisional application No. 61/676,050, filed on Jul. 26, 2012.

(51) Int. Cl.
*C07D 301/10* (2006.01)
*B01J 7/00* (2006.01)
(Continued)

(52) U.S. Cl.
CPC .............. *C07D 301/10* (2013.01); *B01J 7/00* (2013.01); *B01J 21/04* (2013.01); *B01J 23/50* (2013.01); *B01J 23/96* (2013.01); *B01J 35/006* (2013.01); *B01J 35/0013* (2013.01); *B01J 35/1061* (2013.01); *B01J 37/0201* (2013.01); *B01J 37/0203* (2013.01); *B01J 37/08* (2013.01);
(Continued)

(58) Field of Classification Search
CPC ...... C07D 301/10; B01J 7/00; B01J 35/0013; B01J 35/006; B01J 35/1061; B01J 35/1019; B01J 35/1038; B01J 37/08; B01J 37/0203; B01J 37/0201; B01J 38/12; B01J 21/04; B01J 23/50; B01J 23/96
USPC .................................. 549/534; 422/600, 630
See application file for complete search history.

(56) References Cited

U.S. PATENT DOCUMENTS

| 3,563,914 A | 2/1971 | Wattimena |
| 3,702,259 A | 11/1972 | Nielsen |

(Continued)

FOREIGN PATENT DOCUMENTS

WO    WO2008/144409    * 11/2008

OTHER PUBLICATIONS

Drake, L.C., et al., "Macropore-Size Distributions in Some Typical Porous Substances", Ind. Eng. Chem. Anal. Ed., Publication Date: Dec. 1945, 17 (12), pp. 787-791.

(Continued)

*Primary Examiner* — T. Victor Oh
(74) *Attorney, Agent, or Firm* — Scully, Scott, Murphy & Presser, P.C.

(57) ABSTRACT

A method for producing ethylene oxide comprising: providing one or more feed components, wherein the one or more feed components contains at least ethylene obtained by dehydrating ethanol; contacting the one or more feed components with a desulfurization catalyst comprising a high surface area support and an amount of silver, wherein at least 20% of the silver is present as oxidized silver; and contacting the one or more feed components with a silver-containing epoxidation catalyst disposed inside an ethylene oxide reactor to form a reaction gas comprising ethylene oxide.

19 Claims, 2 Drawing Sheets

(51) Int. Cl.

| | | |
|---|---|---|
| | *B01J 37/08* | (2006.01) |
| | *B01J 38/12* | (2006.01) |
| | *B01J 21/04* | (2006.01) |
| | *B01J 23/50* | (2006.01) |
| | *B01J 23/96* | (2006.01) |
| | *B01J 35/00* | (2006.01) |
| | *B01J 37/02* | (2006.01) |
| | *B01J 8/10* | (2006.01) |
| | *B01J 35/10* | (2006.01) |

(52) U.S. Cl.
    CPC .............. *B01J38/12* (2013.01); *B01J 35/1019* (2013.01); *B01J 35/1038* (2013.01)

(56) References Cited

U.S. PATENT DOCUMENTS

| | | |
|---|---|---|
| 4,761,394 A | 8/1988 | Lauritzen |
| 4,766,105 A | 8/1988 | Lauritzen |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,187,140 A | 2/1993 | Thorsteinson et al. |
| 5,407,888 A | 4/1995 | Herzog et al. |
| 2007/0037991 A1 | 2/2007 | Rizkalla |
| 2011/0160470 A1 | 6/2011 | Henstock et al. |
| 2011/0196162 A1* | 8/2011 | Gitter ........................ 549/536 |

OTHER PUBLICATIONS

Brunauer, S., et al., "Adsorption of Gases in Multimolecular Layers", J. Am. Chem. Soc., Feb. 1938, pp. 309-316.

Roscoe, H. E., et al., "A Treatise on Chemistry", The Chemistry of the Hydrocarbons and Their Derivatives, or Organic Chemistry, vol. III, Part 1, 1895, p. 612, New York, D. Appleton and Company, 72 Fifth Avenue.

Amorim De Carvalho, M. C.N., et al., "Study of the active phase of silver catalysts for ethylene epoxidation", Journal of Catalysis 248, Jan. 2007, pp. 124-129, see p. 124.

Ayame, A., et al., "Epoxidation of ethylene over silver catalysts supported on a-alumina crystal carriers", Applied Catalysis A: General 244, May 2003, pp. 59-70, see p. 59.

Kestenbaum, H., et al., "Silver-Catalyzed Oxidation of Ethylene to Ethylene Oxide in a Microreaction System", Ind. Eng. Chem. Res., Publication Date (Web): Jan. 22, 2002, 41, pp. 710-719, see p. 710.

International Search Report dated Nov. 22, 2013 received in a corresponding foreign application.

* cited by examiner

Pulse chemisorption over silver impregnated γ-alumina

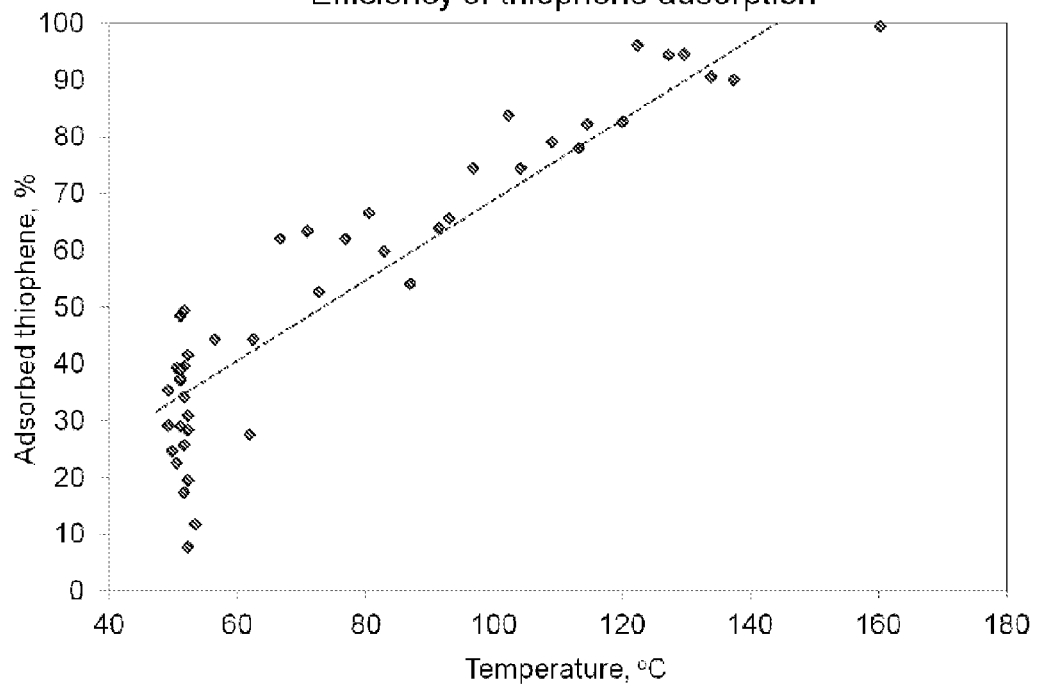

EPOXIDATION PROCESS

RELATED APPLICATION

This application claims benefit of U.S. Provisional Patent Application Ser. No. 61/676,050, filed Jul. 26, 2012, the entire content of which is incorporated herein by reference.

FIELD OF THE INVENTION

The present invention relates to ethylene oxide production and more particularly to a method of producing ethylene oxide in which a feed component including at least ethylene obtained by dehydrating ethanol is first provided and thereafter contacting the feed component with a desulfurization catalyst prior to contacting with a silver-containing epoxidation catalyst.

BACKGROUND OF THE INVENTION

Though present in natural settings at minute quantities, ethylene oxide was first synthesized in a laboratory setting in 1859 by Alsatian chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by French chemist Thèodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 15 billion tons. (About two thirds of the ethylene oxide produced is further processed into ethylene glycol, while about ten percent of manufactured ethylene oxide is used directly in applications such as vapor sterilization.)

The growth in the production of ethylene oxide has been accompanied by continued innovation in catalysis and processing. Recently, and of particular interest to practitioners in the ethylene oxide field has been alternative sources of ethylene feedstock. Conventionally, ethylene is derived from petroleum sources, especially naptha, by thermal cracking with steam. This interest in alternative feedstocks is a result not only of the sustained increase in the price of crude oil but also because of greater environmental consciousness of the importance of using renewable and abundant hydrocarbon sources.

One such renewable hydrocarbon source that has attracted considerable recent interest is bioethanol-derived ethylene. Bioethanol itself is obtained by fermentation of vegetable biomass and agricultural byproducts and wastes—and thus is abundant and renewable. The fermentation of biomass to ethanol results in mixtures containing about 95% water and 5% ethanol. The water is then separated out using a combination of azeotropic distillation or solvent extraction. To produce ethylene the ethanol is then sent to a dehydration process where it is reacted over a dehydration catalyst to from ethylene, which then forms a primary feedstock or feed component for ethylene oxide or one or more ethylene oxide-derivatives. This return to bioethanol for producing ethylene is ironic because when ethylene was first synthesized in the middle of the 19th century, it was obtained by dehydrating ethanol in the presence of a homogeneous phosphorus catalyst. (Roscoe, H. A. and Schorlemmer, C., A *Treatise on Chemistry*, 1878, 612).

While bioethanol-derived ethylene offers the advantage of being an alternative feedstock, abundant and renewable and semi-independent from the world's petroleum market, it also presents certain challenges. Most notably there is the problem that despite attempts to remove impurities and separate byproducts from the bioethanol-derived ethylene, certain contaminants remain that must be treated and removed. For example sulfur-containing compounds, not only the commonly found and relatively-easy-to-remove hydrogen sulfide, but more recalcitrant sulfur-containing compounds such as the refractory organic sulfurs which include, mercaptans, thiophenes, and carbonyl sulfide, are frequently found in bioethanol-derived ethylene. In fact, the presence of sulfur as a byproduct of ethanol dehydration was identified in Roscoe and Schlorlemmer's analytical protocol of the dehydration process—which even specified the use of a caustic scrubbing wash to eliminate it.

As a contaminant sulfur has long been identified as a particularly serious catalyst poison. This is particularly the case for the adsorption of sulfur onto silver, in fact the affinity of silver for sulfur can be seen as the tarnish that visibly forms on silver objects which absorb hydrogen sulfide and other sulfur compounds from the ambient air to form a layer of sulfides. Sulfur is particularly pernicious in an ethylene oxide system as it has long been known as severely and irreversibly poisonous to Ag-based ethylene oxide catalysts (Rebsdat, S. and Mayer D., 2005, *Ethylene Oxide*, Ullmans Encyclopedia of Industrial Chemistry).

A variety of techniques are available to treat hydrocarbon streams containing sulfur-compounds. In adsorptive desulfurization, which is perhaps the easiest and mostly widely used desulfurization technique, the hydrocarbon stream is passed through an adsorbent guard bed to adsorb the sulfur-containing compounds by physical and/or chemical adsorption processes. Most typically, the adsorbent comprises a granular inorganic material such an inorganic oxide; typical examples include zinc oxide, copper oxide, and aluminum oxide but may also be selected from other transition metal oxides and rare earth metal oxides. Preferably guard bed materials are chosen based on their selectivity to adsorbing certain sulfur species, for example copper oxide or zinc oxide are effective at removing simple sulfur compounds, like hydrogen sulfide; while alumina-based adsorbents have some capability for adsorbing organic sulfurs, against which other adsorbing metal oxides are completely ineffectual.

However, while aluminum oxide may be better than zinc oxide for removing organic sulfurs, for many applications it is simply not efficient. Accordingly, other desulfurization techniques, such as hydrodesulfurization may be used instead. In hydrodesulfurization (HDS), a hydrocarbon stream is reacted with hydrogen gas at high temperatures and high pressures over a hydrogenation catalyst. HDS is more effective at removing organic sulfurs than metal oxide adsorbent beds, but it still fails to remove some organic sulfurs. While HDS is more effective than other desulfurization techniques, readily converting mercaptans and thioethers, it fails to convert other organic sulfurs such as substituted and unsubstituted thiophenes. Moreover, HDS is costly and requires high temperatures and pressures.

One alternative to hydrodesulfurization is Oxidative Desulfurization ("ODS"). In ODS a refractory organic sulfur-containing hydrocarbon is contacted with a strong oxidant (such as hydrogen peroxide, an organic peroxide, or organic peracid) in the presence of a metal catalyst, typically one such as titanium, zirconium, chromium, tungsten and molybdenum, to form an organosulfone, which can then be removed by distillation or by further chemical reaction. Compared to hydrodesulfurization, ODS has the advantage of not requiring high temperatures or pressures for operation and ODS removes a fuller spectrum of organic sulfurs than hydrodesulfurization. Thus, ODS has a wider spectrum of refractory organic sulfurs to which it will apply and has less demanding temperature and pressure requirements for reducing the sulfur content in the feedstock sources. However, like HDS, ODS has the disadvantage of being considerably more costly and complicated to implement than a guard bed. The additional complexity not only increases costs but also reduces process flexibility and operability. Additionally ODS requires the provisioning of strong oxidizing agents which are expensive and burdensome to handle.

Given the foregoing there is a continuing need in the art for a desulfurization process that effectively removes a wider spectrum of refractory organic sulfurs than conventional inorganic materials, and yet at the same time can be operated more conveniently with more flexibility and less expensive than conventional hydrodesulfurization and oxidative desulfurization techniques.

SUMMARY OF THE INVENTION

The present invention relates to a method for producing ethylene oxide comprising: a) providing one or more feed components, wherein the one or more feed components contains at least ethylene obtained by dehydrating ethanol; b) contacting the one or more feed components with a desulfurization catalyst comprising a high surface area support and an amount of silver, wherein at least 20% of the silver is present as oxidized silver; and c) contacting the one or more feed components with a silver-containing epoxidation catalyst disposed inside an ethylene oxide reactor to form a reaction gas comprising ethylene oxide.

The present invention also relates to a system for producing ethylene oxide comprising: (a) a source of ethylene obtained by dehydrating ethanol; (b) a desulfurization catalyst comprising a high surface area support and an amount of silver, wherein at least 20% of the silver is present as oxidized silver; (c) an ethylene oxide reactor containing a plurality of reactor tubes; and (d) a silver-containing epoxidation catalyst disposed inside the reactor tubes.

BRIEF DESCRIPTION OF THE DRAWINGS

FIG. 2 is a plot illustrating the temperature dependency of the efficiency of thiophene adsorption using 5% Ag/γ-Al$_2$O$_3$ in accordance with the present invention.

DETAILED DESCRIPTION OF THE INVENTION

Figure 1:
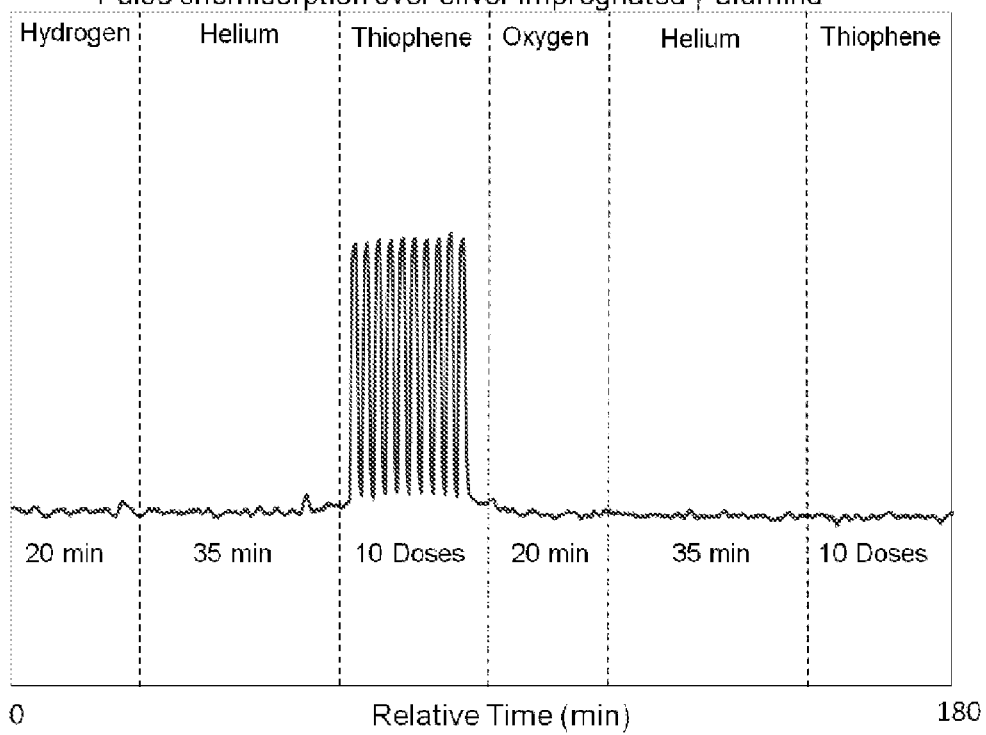
FIG. 1 is a graph illustrating a pulse chemisorption experiment over silver impregnated γ-alumina in accordance with the present invention.

All parts, percentages and ratios used herein are expressed by volume unless otherwise specified. All documents cited herein are incorporated by reference.

As used herein, the terms "refractory organic sulfurs" or "organic sulfurs" include, but are not limited to, at least organosulfur compounds such as carbonyl sulfide (COS), and other sulfides, especially disulfides, mercaptans, thioethers and thiophenes.

It has been found in the present invention that that refractory organic sulfurs may be efficiently and effectively removed from a hydrocarbon stream by contacting the hydrocarbon stream with a desulfurization catalyst, the desulfurization catalyst having an affinity for the sulfur compounds and adsorbing the sulfur onto its surface. A further advantage of the present invention is that this desulfurization is effected by a simple fixed catalyst bed, which can be operated readily and under mild conditions—not adding additional process complexity nor requiring special desulfurization gases. Furthermore, the desulfurization catalyst is renewable in the presence of oxygen and can last for long periods of time without replacement, especially, e.g., for the entire lifespan of a charge of ethylene oxide catalyst. A further advantage of the process of this invention is that the treatment is selective towards the conversion of refractory organic sulfurs and has no apparent effect on feed components containing no refractory organic sulfurs.

The desulfurization catalyst and process of the present invention will be described in greater detail after a brief discussion of the silver-based epoxidation catalyst to be used in the process.

Silver-Based Epoxidation Catalyst

The silver-based epoxidation catalyst that can be employed in the present invention includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention for the silver-based epoxidation catalyst may be selected from a large number of solid, refractory supports that may be porous and may provide the preferred pore structure. Alumina is well known to be useful as a catalyst support for the epoxidation of an olefin and is the preferred support. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The support may comprise at least about 85 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles can preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.)

Suitable supports are available commercially. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 bar to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 hours to 8 hours at a temperature of from 100° C. to 375° C., usually for duration of from about 0.5 hours to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising oxygen, which may be pure oxygen or it may comprise additional components which are inert or non-inert, for example, an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcinations, nitrogen is especially preferred. Further information on catalyst manufacture may be found in the aforementioned U.S. Patent Publication No. 2007/0037991.

Desulfurization Catalyst

The desulfurization catalyst that can be employed in the present disclosure includes a high surface area alumina support upon which is deposited silver. At least part of the silver is present as oxidized silver. By "oxidized silver" it is meant that the silver is present as silver oxide or another form of silver, i.e., the silver is associated with oxygen that can be used for oxidizing sulfur compounds. Preferably more than 20% of the silver present as oxidized silver, more preferably greater than 50% of the silver is present as oxidized silver, most preferably greater than 95% of the silver is present as oxidized silver. In this form, plentiful surface oxygen is present. In one embodiment, the desulfurization catalyst contains substantially no alkali metals. By "substantially no alkali metals" it is meant that no alkali metals are deliberately deposited on or included in the desulfurization catalyst, although trace amounts may be present as a result of manufacture or present from precursor material.

In a separate embodiment, the desulfurization catalyst consists essentially of an alumina support, and an amount of silver, at least part of which is oxidized silver, wherein the basic and novel properties of the desulfurization catalyst is its efficacy in adsorbing and removing refractory organic sulfurs from hydrocarbon-containing streams.

The high surface area alumina support has the following characteristics:

Average pore size: less than 30 nm;

BET surface area: greater than 100 $m^2/g$, preferably the BET surface area is between 100 $m^2/g$ and 400 $m^2/g$;

Pore Volume: greater 0.4 $cm^3/g$, preferably the pore volume is between 0.7 $cm^3/g$ to 1.2 $cm^3/g$;

Silver particle size: less than 50 nm, preferably less than 20 nm, more preferably less than 10 nm.

In one embodiment of the present invention, the high surface area alumina is preferably selected from alumina hydroxides, alumina oxide hydroxides and alumina oxides. An especially preferred alumina oxide hydroxide is boehmite. An especially preferred alumina oxide is gamma-alumina.

As used herein, the "pore diameter" is used interchangeably with "pore size". The pore volume (and pore size distribution) described herein can be measured by any suitable method, but are more preferably obtained by the conventional mercury porosimeter method as described in, for example, Drake and Ritter, *Ind. Eng. Chem. Anal. Ed.*, 17, 787 (1945). The B.E.T. surface area described herein can be measured by any suitable method, but is more preferably obtained by the method described in Brunauer, S., et al., *J. Am. Chem. Soc.*, 60, 309-16 (1938).

The desulfurization catalyst is prepared (especially in the impregnation and calcinations stages) in the same method as described above for the ethylene oxide catalyst. Preferably the desulfurization catalyst is prepared in a process which includes, at least, impregnating a high surface area alumina support with an ammonia oxalate impregnating solution containing at least silver and calcined in a nitrogen atmosphere. Preferably, the catalyst produced by this process has less than 100 ppm sodium.

It is important to manage the oxidized silver on the catalyst properly over extend usage—i.e., over the typical lifespan of an ethylene oxide catalyst. The desulfurization catalyst of the present invention readily adsorbs sulfur and so during the course of extended use, continuous exposure to sulfur-containing hydrocarbons, particularly when exposed to atmospheres rich in sulfur-containing hydrocarbon but with only with limited oxygen content (as may be the case in an ethylene oxide (EO) reactor when the ethylene contains high quantities of sulfur) impairs the performance and efficacy of the desulfurization catalyst. Without being limited by theory, while the loss of performance can be attributed in part to excessive sulfur adsorption in the silver layer of the catalyst, it is, however, believed that this loss of performance is caused especially by loss of oxygen from the catalytically active silver sites. In order to replenish the oxygen-depleted areas, it is necessary to regenerate the desulfurization catalyst by exposing the catalyst to oxygen or an oxygen source such as air, which allows the adsorption of oxygen into the silver to replenish the oxygen-depleted areas and restored the silver to the form of oxidized silver.

The need for regeneration thus dictates the configuration and placement of the desulfurization catalyst—specifically, the desulfurization catalyst must be placed in fluid communication with a source of oxygen.

Epoxidation Process and Reactor System

The epoxidation process is carried out in a reactor system according to the present invention by continuously contacting an oxygen-containing gas with ethanol-derived ethylene in the presence of an epoxidation catalyst to form ethylene oxide and byproducts. The preparation of ethylene according to the present invention starts with the provision of ethanol. (This ethanol is preferably produced from biomass material ("bioethanol") or some other abundant and renewable source of ethanol, however, ethanol obtained from any source is acceptable.) Having provisioned the ethanol, the ethanol is then vaporized by steam and further pre-heated to a suitable reaction temperature in a furnace. The pre-heated vaporized ethanol is then passed to a dehydration reactor where it is converted to ethylene as it passes over the dehydration catalyst. Oxygen may be supplied to the reaction in substantially pure molecular form or in a mixture such as air. By way of example, the one or more feed components in the feed mixtures may contain from about 0.5% to about 45% ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. The one or more components of the reaction feed mixture enter the reactor via one or more inlets which are in fluid communication with the source of the components and said inlets are also in fluid communication with the upper ends of the reaction tubes (discussed in greater detail, below). Carbon dioxide and water are byproducts of the epoxidation process as well as common contaminants in the feed gases. Both have adverse effects on the catalyst, so the concentrations of these contaminants are usually kept at a minimum.

As mentioned above, sulfur is also a contaminant whose concentration in the reactor feed mixture must be minimized. In the present invention, this is done by contacting the reactor feed mixture with the desulfurization catalyst. In one specific embodiment, the desulfurization zone, containing a fixed bed of desulfurization catalyst, is itself contained in a desulfurization chamber. The desulfurization chamber is located upstream from and outside of the reactor so that refractory organic sulfur compounds are removed from the feed components before they enter the reactor and contact the silver ethylene oxide catalyst and poison it. One or more feed components of the ethylene oxide reactor are communicated and enter into the desulfurization chamber, are treated, and then exit the desulfurization chamber and are communicated to the reactor. The desulfurization chamber is also placed in communication with a heat source and pressure source to allow operation at elevated temperature and pressure. Preferably, the one or more feed components contacts the desulfurization catalyst at a temperature in the range of from about 40° C. to about 400° C., preferably from about 80° C. to about 300° C., more preferably from about 150° C. to about 185° C. Generally, the performance and efficiency of the desulfurization catalyst improves with increasing temperature up to a maximum service temperature; the material of the present invention has an efficiency factor of about 0.6%/° C. to about 0.8%/° C. illustrating the improvement of efficiency of removing refractory sulfurs with increasing temperature. More preferably, the material of the present invention has a thiophene efficiency factor of about 0.6%/° C. to about 0.8%/° C. The aforementioned efficiency factor is determined by measuring the amount of an organic sulfur absorbed at a particular temperature and then repeating such measurement, under identical conditions, for several different temperatures. These data points are then plotted on a two dimensional grid with the Y-axis representing the amount of absorbed thiophene and the X-axis representing the temperature. Using a least-squares or other such suitable method, a straight line is fit to the data and this straight line is the efficiency factor for the material.

However, although the desulfurization catalyst becomes more efficient with increasing temperatures the operator may nonetheless prefer to operate it in the lower temperature ranges recited above, especially because there are the normal operating temperatures of the epoxidation process.

Preferably, the one or more feed components contacts the desulfurization catalyst at a pressure in the range of from about 0 atm to about 50 atm, preferably from about 1 atm to about 35 atm, more preferably from about 1 atm to about 25 atm.

The sulfur removal unit may also include analyzers to measure the sulfur level in the ethylene as it enters and exits the sulfur removal unit. This analyzer is preferably an online analyzer.

A valve may be used to allow the desulfurization chamber to be selectively coupled to the one or more feed components. The valve may be operated manually or automatically. In addition, a bypass line may be provided around the desulfurization chamber. By using the valve and the bypass line, a process user may selectively connect or disconnect the one or more feed components to the desulfurization chamber. Among the one or more feed components communicated to the reactor includes at least 25%, preferably at least 50%, more preferably at least 90% of the total ethylene feed (on a time average basis) that is communicated to the ethylene oxide reactor is contacted upstream of the ethylene oxide reactor by the desulfurization catalyst. If neither oxygen nor an oxygen source is among the one or more feed components communicated to the reactor, then the reaction chamber must include a separate inlet for communicating oxygen or an oxygen source into the reaction chamber to allow regeneration of the desulfurization catalyst.

Multiple desulfurization chambers may also be used either in series or in parallel. A suitable example of a parallel configuration is the swing-bed configuration. This configuration includes two swing-bed desulfurization chambers capable of alternating between adsorption mode and regeneration mode. In adsorption mode, the desulfurization chamber is in communication with one or more feed components to remove the organic refractory sulfurs and the one or more feed components are then communicated to the reactor. In regeneration mode, the desulfurization chamber is in communication with only an oxygen-source in order to regenerate the desulfurization catalyst inside. The desulfurization chambers may also be connected in series. In one embodiment of the series configuration, multiple desulfurization chambers are connected, wherein each desulfurization chamber has a different absorbent material that is selective to different species of sulfur-containing compounds.

Other of the one or more components of the reaction feed mixture includes one or more chlorine moderators non-limiting examples of which include organic halides such as $C_1$ to $C_8$ halohydrocarbons; especially preferred methyl chloride, ethyl chloride, ethylene dichloride, vinyl chloride or mixtures thereof. Also suitable are hydrogen-free chlorine sources such as perhalogenated hydrocarbons and diatomic chlorine are particularly effective as moderators in gas phase epoxidation. Perhalogenated hydrocarbons refer to organic molecules in which all of the hydrogen atoms in a hydrocarbon have been substituted with halogen atoms; suitable examples are trichlorofluormethane and perchloroethylene. It is important that the concentration level of the moderator be controlled so as to balance a number of competing performance characteristics; for example, moderator concentration levels that result in improved activity may simultaneously lower selectivity. Controlling moderator concentration level is particularly important with the rhenium-containing catalysts of the present invention, because as the rhenium-containing catalysts age the moderator concentration must be carefully monitored so as to continually increase, within very small increments, because optimal selectivity values are obtained only within a narrow moderator concentration range.

In a separate embodiment, the desulfurization catalyst is disposed directly in the catalyst tubes. In this embodiment, the reactor tubes contain a packed ethylene oxide catalyst bed and a desulfurization catalyst zone formed above, upstream of the ethylene oxide catalyst bed possibly even formed directly on top of the ethylene oxide catalyst bed. In this configuration the desulfurization catalyst is closer to the upper end of the reaction tube and is upstream from the ethylene oxide catalyst bed which is closer to the lower end of the reaction tube. (The configuration of the reactor and reactor tubes is discussed in greater detail, below). The desulfurization catalyst being upstream of the intermediate ethylene oxide catalyst bed removes the refractory organic sulfur compounds from the reaction mixture before the sulfur can "see" the silver ethylene oxide catalyst. Additionally, as oxygen is a component of the reaction mixture, it is not necessary to provide an additional source of oxygen; in this embodiment, substantially all of the ethylene feed is contacted by the desulfurization catalyst. In this embodiment the desulfurization catalyst is preferably formed in a packed catalyst bed.

As a result of contacting the one or more components with the desulfurization catalyst, in any of the aforementioned embodiments, the concentration of organic refractory sulfurs in the reaction mixture that is fed into the reactor is reduced, although it will not be reduced to concentrations of zero sulfur content. Specifically, the concentration of the total sulfur in the reactor feed mixture (including all sulfur types and species) after passing through the desulfurization catalyst is not more than about 2 ppmv, more preferably not more than about 1 ppmv, even more preferably not more than about 100 ppbv, with concentrations of not more than about 50 ppbv being most preferred.

A usual method for the ethylene epoxidation process comprises the vapor-phase oxidation of ethylene with molecular oxygen, in the presence of the catalyst, in a fixed-bed tubular reactor. Conventional, commercial fixed-bed ethylene-oxide reactors are typically in the form of a shell and tube heat exchanger containing plurality of parallel elongated tubes in a suitable shell, each tube being approximately 0.7 to 2.7 inches O.D. and 0.5 to 2.5 inches I.D. and 15-53 feet long filled with silver-based epoxidation catalyst, desulfurization catalyst, and other optional components such as inerts. The reactor will likely contain a plurality of reactor tubes, likely several thousand tubes and as many as twenty thousand. Upper and lower tube sheets are provided to support the multiplicity of tubes, the upper tube sheet being located at the upper end each reactor tube, and the lower tube sheet being located at the lower end of each reactor tube. In practice, feed components in the form of reaction gases, e.g., ethylene, oxygen, ballast gas (and other aforementioned feed components) are introduced into the reactor through one or more reactor inlets, enter through an upper inlet head located adjacent to the upper end of the reactor tubes and pass at reaction conditions through reactor tubes which are packed with an appropriate silver catalyst. Heat of reaction is removed by a circulating heat transfer fluid such as water which is introduced to the shell side of reactor. Olefin oxide, un-used reactants, and byproducts exit the reactor through a reactor outlet.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 seconds to about 20 seconds.

The resulting ethylene oxide, which exits the reactor through the reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts including carbon dioxide.

The previously-described silver-based catalysts have been shown to be particularly selective for oxidation of ethylene with molecular oxygen to ethylene oxide especially at high ethylene and oxygen conversion rates. The conditions for carrying out such an oxidation reaction in the presence of the silver-based catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 10-25 atm, a coolant temperature of 180-315° C., an oxygen conversion level of 10-60%, and an EO production rate (work rate) of 7-20 lbs. EO/cu·ft·catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

EXAMPLES

Example 1

A pulsed chemisorption experiment was employed in the present invention to show the dependence of oxygen to activate and reactivate the sulfur adsorption capacity of refractory compounds by the adsorbent material disclosed.

About 2 grams of the desulfurization catalyst prepared as described previously (5% silver deposited on a gamma alumina carrier having a surface area of approximately 200 $m^2/g$) but not oxidized with an oxidizing gas was loaded into a test cell and heated to 255° C. Once the temperature was stabilized under an inert gas (in this case, helium) the sample was exposed to a reducing gas, hydrogen (5% in ultra high purity argon) for 20 minutes. A 35 minute helium purge was performed to ensure any physisorbed hydrogen was removed. After clearing the sample and sample chamber with helium gas, thiophene was pulsed over the sample. The sample was exposed to ten pulses of 1 cc volume of 21 ppm of thiophene, with the balance being helium. The thiophene pulses demonstrated complete breakthrough of the thiophene over the hydrogen-reduced silver adsorbent as shown by the spikes in thiophene concentration in the first thiophene region, shown in FIG. 1. This demonstrated that when the silver in the defulurization catalyst was not oxidized it was not effective at removing refractory sulfurs such as thiophene. The sample was then treated with an oxidizing gas-oxygen (10% in ultra high purity helium) for 20 minutes. The desulfurization catalyst sample and chamber was flushed with helium for 35 minutes to ensure any physisorbed oxygen was removed before introducing thiophene. The oxidized form of the silver adsorbent completely adsorbed the thiophene pulsed over the sample, as shown in the second thiophene zone of FIG. 1. Thus, a desulfurization catalyst prepared according to the present invention and exposed to an oxidizing gas was far superior at absorbing a refractory sulfur such as thiophene.

Example 2

A pulsed chemisorption experiment was employed to show how the efficiency of the desulfurization catalyst is dependent on temperature. The figure also illustrates the optimum range of operating temperatures. The same desulfurization catalyst as in Example 1 was used. And the experiment was conducted with the same test cell and operating protocol as in Example 1. However, in this experiment, the desulfurization catalyst was first heated to 50° C. in a helium atmosphere and held at temperature for 15 minutes. During this period, thiophene was introduced into the chamber containing the desulfurization catalyst with a constant flow. The gas consisted of 21 ppm thiophene in an ultra high purity helium balance. As it can be seen in FIG. 2, the material demonstrated a slow uptake of thiophene, even at 50° C., with a limited efficiency of 30% of the total concentration. The sample was then heated at a ramp rate of 10° per minute, from 50° C. to 150° C. and 46 measurements of the adsorbed thiophene made. The measured adsorbed thiophene was as follows:

TABLE I

Temperature Dependency of the Efficiency of Thiophene adsorption using 5% Ag/γ-$Al_2O_3$

| No. | Temp | Thiophene abs |
|---|---|---|
| 1 | 52.3 | 7.8 |
| 2 | 53.5 | 11.7 |
| 3 | 51.7 | 17.4 |
| 4 | 61.9 | 27.5 |
| 5 | 51.7 | 25.7 |
| 6 | 50.5 | 22.6 |
| 7 | 51.1 | 29.1 |
| 8 | 51.7 | 34.1 |
| 9 | 52.3 | 19.6 |
| 10 | 52.3 | 30.9 |
| 11 | 51.7 | 39.5 |
| 12 | 52.3 | 28.3 |
| 13 | 51.1 | 37.1 |
| 14 | 51.1 | 37.5 |
| 15 | 49.3 | 29.2 |
| 16 | 50.5 | 39.3 |
| 17 | 51.1 | 39.1 |
| 18 | 51.1 | 48.4 |
| 19 | 51.7 | 49.3 |
| 20 | 52.3 | 41.5 |
| 21 | 49.3 | 35.3 |
| 22 | 49.9 | 24.7 |
| 23 | 56.5 | 44.4 |
| 24 | 62.5 | 44.4 |
| 25 | 66.7 | 62.0 |
| 26 | 70.9 | 63.3 |
| 27 | 72.7 | 52.7 |
| 28 | 76.9 | 62.0 |
| 29 | 80.5 | 66.5 |
| 30 | 82.9 | 59.9 |
| 31 | 86.9 | 54.1 |
| 32 | 91.3 | 63.9 |
| 33 | 93.0 | 65.5 |
| 34 | 96.8 | 74.5 |
| 35 | 102.3 | 83.8 |
| 36 | 104.1 | 74.4 |
| 37 | 109.0 | 79.1 |
| 38 | 114.5 | 82.3 |
| 39 | 113.3 | 78.0 |
| 40 | 120.0 | 82.7 |
| 41 | 122.4 | 96.1 |
| 42 | 127.2 | 94.4 |
| 43 | 129.6 | 94.6 |
| 44 | 133.8 | 90.6 |
| 45 | 137.4 | 90.0 |
| 46 | 141.0 | 102.3 |

These results set forth in Table 1, above, are plotted in FIG. 2. The straight line (plotted by least squares method) shows that this desulfurization catalyst has an efficiency factor of 0.71% per ° C.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

What we claim is:

1. A method for producing ethylene oxide comprising:
 a) providing one or more feed components, wherein the one or more feed components contains at least ethylene obtained by dehydrating ethanol;
 b) contacting the one or more feed components with a desulfurization catalyst comprising a high surface area support and an amount of silver, wherein at least 20% of the silver is present as oxidized silver; and
 c) contacting the one or more feed components with a silver-containing epoxidation catalyst disposed inside an ethylene oxide reactor to form a reaction gas comprising ethylene oxide.

2. The method according to claim 1, wherein the one or more feed components further comprises oxygen and a ballast gas.

3. The method according to claim 1, wherein the process further comprises contacting the one or more feed components with the desulfurization catalyst at a temperature in a range of from about 40° C. to about 400° C.

4. The method according to claim 1, wherein the process further comprises contacting the one or more feed components with the desulfurization catalyst at a pressure in a range of from 0 atm to 50 atm.

5. The method according to claim 1, wherein the process further comprises contacting the one or more feed components with said desulfurization catalyst positioned inside a desulfurization chamber that is located outside the ethylene oxide reactor.

6. The method according to claim 1, wherein the ethylene oxide reactor contains one or more reaction tubes packed with a bed of said desulfurization catalyst and a bed of said silver-containing epoxidation catalyst.

7. The method according to claim 1, further comprising regenerating the desulfurization catalyst.

8. The method according to claim 1, wherein the high surface area-alumina support has a surface area of greater than about 100 $m^2$/g.

9. The method according to claim 8, wherein the high surface area alumina is selected from gamma alumina and boehmite.

10. The method according to claim 1, wherein the desulfurization catalyst comprises about 0.1 wt % to about 30 wt % silver.

11. The method according to claim 1, wherein the one or more feed components in step (c) has a sulfur concentration of not more than about 2 ppmv.

12. The method according to claim 1, wherein the desulfurization catalyst contains substantially no alkali metal.

13. The method according to claim 1, wherein the ethylene is obtained by dehydrating ethanol in a dehydration reactor.

14. The method according to claim 1, wherein the catalyst has less than 100 ppm sodium.

15. The method according to claim 1, wherein the desulfurization catalyst is prepared in a process including at least the steps of impregnating a high-surface area alumina support with an ammonia oxalate impregnating solution containing at least silver; and calcining in a nitrogen atmosphere.

16. The method according to claim 1, wherein the desulfurization catalyst has an efficiency factor of about 0.6%/° C. to about 0.8%/° C.

17. The method according to claim 1, wherein at least 50% of the silver is present as oxidized silver.

18. The method according to claim 1, wherein the desulfurization catalyst consists essentially of: (1) an alumina support, and (2) an amount of silver; wherein at least 20% of the silver is present as oxidized silver.

19. The method according to claim 8, wherein the high surface area alumina is selected from alumina hydroxides, alumina oxide hydroxides and alumina oxides.

\* \* \* \* \*